United States Patent [19]

Wille

[11] 3,991,105

[45] Nov. 9, 1976

[54] PROCESS FOR THE PREPARATION OF 3-ACETAMIDO-5-AMINO-2,4,6-TRIIODOBENZOIC ACID

[75] Inventor: Knut Wille, Osteras, Norway

[73] Assignee: Nyegaard & Co. A/S, Oslo, Norway

[22] Filed: May 17, 1974

[21] Appl. No.: 470,926

[30] Foreign Application Priority Data

May 18, 1973 United Kingdom............ 23872/73

[52] U.S. Cl............................................. 260/518 A
[51] Int. Cl.$^2$..................................... C07C 101/68
[58] Field of Search................................. 260/518 A

[56] References Cited
UNITED STATES PATENTS

| 2,895,988 | 7/1959 | Archer et al.............. | 260/518 A |
| 3,133,116 | 5/1964 | Larson...................... | 260/518 A |
| 3,647,864 | 3/1972 | Ackerman................. | 260/518 A |
| 3,734,953 | 5/1973 | Bernstein et al........... | 260/518 A |

FOREIGN PATENTS OR APPLICATIONS 990,757   4/1965   United Kingdom

Primary Examiner—Anton H. Sutto
Attorney, Agent, or Firm—Bacon & Thomas

[57] ABSTRACT

The invention provides a process for the preparation of 3-acetamido-5-amino-2,4,6-triiodobenzoic acid substantially free from diiodinated material, in which 3-acetamido-5-aminobenzoic acid or a salt thereof is gradually introduced into an aqueous acid system which contains an excess of iodine chloride (ICl) in a stabilized form. In particular, the gradual introduction of 3-acetamido-5-aminobenzoic acid may be achieved by using 3,5-diacetamidobenzoic acid as starting material, the acid medium effecting hydrolysis of one acetamido group and the excess iodinating reagent reacting selectively at such a rapid rate that the desired triiodinated product is formed and precipitated without further hydrolysis or premature precipitation of unwanted diiodinated products.

10 Claims, No Drawings

PROCESS FOR THE PREPARATION OF 3-ACETAMIDO-5-AMINO-2,4,6-TRIIODOBENZOIC ACID

This invention relates to a process for the manufacture of a key intermediate in the synthesis of metrizoic acid and related X-ray contrast agents, namely 3-acetamido-5-amino-2,4,6-triiodobenzoic acid.

In order to produce asymmetrically substituted 3,5-diamino-2,4,6-triiodobenzoic acids, such as metrizoic acid, various multi-stage processes have been suggested which require, at some stage, a selective reaction such as partial reduction of 3,5-dinitrobenzoic acid or partial acetylation of 3,5-diamino-benzoic acid. Such selective reactions, required to produce the desired asymmetry, are difficult or inefficient as compared with straightforward unselective reactions and thus in general add considerably to the overall cost of the manufacture.

Additional problems arise with triiodination of some 3,5-diamino-benzoic acid derivatives in that the first two iodine atoms may be introduced without difficulty, but a substantial proportion of the diiodo compounds so produced tends to remain as a contaminant of the desired triiodo product. Consequently the yield and purity of the latter are often undesirably low. Thus, British Patent Specification No. 990,757 describes a process for triiodination of 3-acetamido-5-aminobenzoic acid in which the diiodo compound is prepared initially and subsequently further iodinated under specially selected conditions. This process has been found, however, to give as much as 10% diiodo material as contaminant and this is extremely difficult to remove economically.

It has now been found that if the 3-acetamido-5-aminobenzoic acid is introduced into a system which always contains an excess of iodinating agent, at such a rate that its concentration in the medium is kept low, it is possible to produce the triiodinated product in very good yields substantially free of any contaminating diiodinated intermediate. It is believed that the low concentration of the starting compound restricts the concentration of the initial diiodinated product to within its solubility limit, so permitting the third iodine atom to be introduced. It is thought that the previously observed high percentage of diiodinated contaminant was due to its concentration exceeding the solubility limit and the resulting precipitation preventing the final iodination.

According to the present invention there is provided a process for the preparation of 3-acetamido-5-amino-2,4,6-triiodobenzoic acid substantially free from diiodinated material, in which 3-acetamido-5-aminobenzoic acid or a salt thereof is gradually introduced into an aqueous acid system which contains an excess of iodine chloride (ICl) in a stabilised form.

The gradual introduction of 3-acetamido-5-aminobenzoic acid required in the new process may be achieved by direct gradual addition of the 3-acetamido-5-amino-benzoic acid or a salt thereof or, as is explained in detail below, indirectly by in situ conversion of an alternative starting material at a relatively slow rate.

In general, the higher the temperature the faster the iodine chloride will react, but higher temperatures may also cause decomposition of the iodine chloride and so an excess should in such cases desirably be added to compensate for this. Naturally, the faster the triiodination reaction, the faster the starting material may be introduced. The temperature should desirably be at least 55° C, preferably 60°–100° C, advantageously 70°–95° C particularly good results being obtained in the range 80°–90° C.

The iodine chloride should be in a stablised form; this being achieved, for example, by using a relatively high concentration of acid, e.g. hydrochloric acid, for example, about 5% concentration, or by using a stable complex, e.g. an alkali metal chloride/ICl complex such as $NaICl_2$ or $KICl_2$. In general, the complex should be neutral or acidic.

The aqueous system should be acid as stated above, and in general the strong inorganic acids such as hydrochloric, sulphuric, phosphoric, nitric or perchloric acid may be used. The concentration of acid should desirably not be too high, however, or contaminating products may be produced; thus a pH of below 2, but preferably in the range 1 to 0, is desirable.

The initial concentration of ICl is advantageously in the range 40 to 120g/litre, preferably 50 to 100g/litre. A slight excess over the stoichiometric quantity required for triiodination is desirable, for example a 5 to 15% excess.

The optimal rate of introduction of 3-acetamido-5-aminobenzoic acid depends on the other reaction parameters but is preferably 0.1 to 0.5, more preferably 0.15 to 0.25g/litre reaction medium/minute.

The reaction medium is essentially water. Addition of water-miscible solvents is unnecessary and not generally desirable in that the relative solubilities of the reactants, end product and transient intermediates may not then be favourable. However, some acetic acid may be present in the starting material, although normally in small quantities.

Particularly good results have been obtained, surprisingly, by indirect introduction of 3-acetamido-5-aminobenzoic acid using 3,5-diacetamidobenzoic acid as starting material, since, under the acid iodinating conditions it undergoes partial hydrolysis whereby the initially formed 3-acetamido-5-aminobenzoic acid is gradually introduced into the medium and immediately iodinated in situ to form the desired 2,4,6-triiodo compound which being precipitated from solution, is not further hydrolysed under the conditions prevailing. Being symmetrically substituted, 3,5-diacetamidobenzoic acid is much more easily obtained, and is hence much cheaper, than 3-acetamido-5-amino-benzoic acid.

In a typical reaction of this indirect type, 3,5-diacetamido-benzoic acid is reacted at elevated temperatures in suspension in aqueous acid with an excess of iodine chloride in a stablised form, e.g. an alkali metal halide complex.

Preferably, the reactants are mixed in the cold and heated to the required temperature. Using this technique, high yields of 3-acetamido-5-amino-2,4,6-triiodobenzoic acid have been obtained containing very low concentrations of contaminating diiodinated material.

Since in this indirect process hydrolysis of one acetamido group is essential, the pH of the aqueous system should preferably be at the lower end of the range mentioned earlier. However, high acid concentrations require care to avoid production of contaminating products. In general the pH is advantageously in the range 1.0 to 0.1.

The reaction temperature in the indirect process is desirably such that the iodination, especially the introduction of the third iodine atom, is as rapid as possible, while the hydrolysis is not too rapid or too slow and the iodine chloride does not decompose unduly. In general a temperature of from 60° C to 100° C is advantageous but at 60° C–70° C a considerable proportion of unreacted 3,5-acetamido benzoic acid may be recovered unless reaction time is relatively long It is preferable to operate at a temperature of 65° C to 100° C, advantageously 80° C to 95° C, especially about 85° C.

The 3,5-diacetamidobenzoic acid starting material used in the indirect hydrolytic process may be prepared by diacetylation of 3,5-diaminobenzoic acid, e.g. by reaction with acetic anhydride in an aqeuous medium. The resulting products in the aqueous medium, which contains acetic acid deriving from the acetylating reagent, may be used directly in the triiodination simply by addition of dilute acid and iodinating agent followed by heating to an appropriate reaction temperature.

3-Acetamido-5-amino-2,4,6-triiodobenzoic acid can be converted into metrizoic acid or an analogue thereof by N-alkylation, e.g. to form a 3-N-alkylacetamido-5-amino-triodobenzoic acid and subsequent acetylation, as described in our British Patent Specification No. 973,881. Thus, treatment with dimethyl sulphate under alkaline conditions followed by treatment with acetic anhydride under strongly acid conditions yields metrizoic acid itself.

The following Examples illustrate the invention further – all temperatures are in ° C.

TLC was performed on Silica gel $F_{254}$ (precoated plates from Merck AG) and developed in
A. Ethyl acetate:butanol-(1) : glacial acetic acid (100 : 20 : 5) and
B. Chloroform : diethyl ether : formic acid: methanol (55 : 25 : 10 : 10):-

Iodination of 3,5-diacetamidobenzoic acid

A. General procedure for Examples 1–9

3,5-Diacetamidobenzoic acid (3.0 g, 12.7 mmole) was suspended in water or dilute acid (60ml), pH adjusted to the wanted value and then 3.7M $NaICl_2$ (12 ml, 44.4 mmole) was added and the reaction flask set in a preheated oil bath. When the reaction was finished, the reaction mixture was cooled to room temperature and stirred for several hours before filtration. The product was suspended in water acidified with hydrochloric acid, filtered off and dried at 50° in vacuo. It may be mentioned that an aqueous suspension of 3,5-diacetamidobenzoic acid gives pH 3.4 – 3.7 and a suspension of the acid in 0.2N HCl gives pH of about 0.7.

B. Slow addition of sodium 3,5-diacetamidobenzoate

Example 10

A mixture of dilute hydrochloric acid (60 ml) with pH about 0.2 and 3.7M $NaICl_2$ (12 ml) was heated at 80°–90°. Then a solution of sodium 3,5-diacetamidobenzoate (3.3 g, 12.7 mmole) in water (10 ml) was added through a dropping funnel during 50 minutes. After 3½ hours, the reaction mixture was cooled to room temperature and stirred for several hours before filtration. The product was suspended in water acidified with hydrochloric acid and then collected on a filter. Yield: 5.2 (71%).

IODINATION OF 3-ACETAMIDO-5-AMINOBENZOIC ACID

A. Addition of sodium 3-acetamido-5-aminobenzoate

General procedure for Examples 11–13

A mixture of diluted hydrochloric acid (60 ml) with pH about 0.2 and 3.70M $NaICl_2$ (12 ml, 44.4 mmole) was heated at the wanted temperature and then a solution of sodium 3-acetamido-5-aminobenzoate (2.7 g, 12.5 mmole) in water (10 ml) was added through a dropping funnel. The times of addition are given in Table 2. The reaction mixtures were heated for 5–10 minutes after the additions were finished. After cooling to room temperature the mixtures were stirred for several hours before filtration. Then the products were suspended in water acidified with hydrochloric acid, filtered off and dried at 50° in vacuo.

B. Addition of 3-acetamido-5-aminobenzoic acid

Example 14 was performed as given in A, but 3-acetamido-5-aminobenzoic acid was added as a solid in small portions during 1 hour.

In both tables the colum "chromatographic quality" refers to the presence of unwanted by-products. In each case the more X's the purer the sample is.

EXAMPLE 15

Preparation of 3-acetamido-5-amino-2,4,6-triiodobenzoic acid from 3,5-diaminobenzoic acid via 3,5-diacetamidobenzoic acid.

3,5-Diaminobenzoic acid (60.8 g, 0.4 mol) was suspended in water (3 litres), heated to 70°–75° C and acetylated by dropwise addition of acetic anhydride (100 ml, 1.0 mol). The reaction mixture was stirred for 1 hour at 70°–75° C and then cooled to room temperature. Thin-layer chromatography showed that all 3,5-diaminobenzoic acid had reacted; the obtained 3,5-diacetamidobenzoic acid contained about 2% of 3-acetamido-5-aminobenzoic acid.

The reaction mixture was diluted with 2N hydrochloric acid (1150 ml) and 3.7M $NaICl_2$-solution (333 ml). The mixture was heated to 86° C and kept at this temperature for 2 hours with good stirring. Excess of ICl was reduced by addition of $Na_2S_2O_5$ at room temperature and the 3-acetamido-5-amino-2,4,6-triiodobenzoic acid was filtered off and washed with water after stirring for 8 hours.

Yield 195 g (85%).

The crude product was suspended in water (600 ml) and dissolved by addition of sodium hydroxide solution (pH about 9). The solution was heated to about 80° C, decolourized by addition of about 2g of $Na_2S_2O_4$ and then $NH_4Cl$ (about 100 g) was added. The pH was adjusted to about 7.5 by addition of ammonia. After stirring for 12–15 hours in a cold water bath the precipitated ammonium salt of 3-acetamido-5-amino-2,4,6-triiodobenzoic acid was filtered off, washed with a 20% ammonium chloride solution. The ammonium salt was suspended in water, dissolved by addition of sodium hydroxide solution and the acid precipitated by addition of hydrochloric acid, filtered, washed with water and dried at 70° C.

Overall yield: 180g(78.5%); I 65.6%; N 4.7%; Calculated for $C_9 H_7I_3N_2O_3$: I 66.6%; N 4.9%.

The product contained 0.3% of diiodo compounds.

Treatment of a solution of the product in aqueous KOH with 1.82 equivalents of dimethyl sulphate and subsequent acidification yields 3-(N-methyl)-acetamido-5-amino-2,4,6-triiodobenzoic acid (97%) which when suspended in acetic anhydride, warmed, acidified with conc. sulphuric acid, refluxed, partially evaporated and cooled, yields metrizoic acid.

ide are mixed cold in an aqueous acid suspension and the mixture is then heated.

7. A process as claimed in claim 1 in which the reaction is effected at a temperature of 80° to 95° C.

8. A process as claimed in claim 1 in which the reaction medium is essentially water.

9. A process as claimed in claim 1 in which dilute

Table 1:

Iodination of 3,5-diacetamidobenzoic acid.

| Method | No. | Acid | pH | React. temp. °C | React time h | Yield % | Diiodo compd. % | Unreact. starting material | Chromatographic quality |
|---|---|---|---|---|---|---|---|---|---|
| A | 1 | $H_2SO_4$ | 0.95 | 95–100 | 4 | 80 | 0.5 | 0.5 | xxxx |
| A | 2 | HCl | 0.80 | 95–100 | 4 | 71 | 0.5 | 0.5 | xxxx |
| A | 3 | $HNO_3$ | 0.70 | 95–100 | 4 | 74 | 0.5 | 0.5 | xxxx |
| A | 4 | $HClO_4$ | 0.60 | 95–100 | 4 | 73 | 0.5 | 0.5 | xxxx |
| A | 5 | $H_3PO_4$ | 0.65 | 95–100 | 4 | 75 | 0.5 | 0.5 | xxxx |
| A | 6 | $H_2SO_4$ | 0.22 | 95–100 | 4 | 69 | 0.5 | 0.5 | xxxx |
| A | 7 | HCl | 0.22 | 95–100 | 4 | 64 | 0.5 | 1 | xxxx |
| A | 8 | $H_2SO_4$ | 0.20 | 80–90 | 3 | 75 | 0.5 | 0.5 | xxxx |
| A | 9 | HCl | 0.20 | 80–90 | 5 | 64 | 0.5 | 1 | xxxx |
| B | 10 | HCl | 0.2 | 80–90 | 3½ | 71 | — | 2–3 | xxx(x) |

Table 2:

Iodination of 3-acetamido-5-aminobenzoic acid

| Method | No. | Acid | pH | React temp °C. | React time min. | Yield % | Diiodo comp. % | Unreact. starting material % | Chromatographic quality | Time for addition (min) |
|---|---|---|---|---|---|---|---|---|---|---|
| A | 11 | HCl | 0.2 | 80–90 | 35 | 79 | 1 | <0.5 | xxx | 30 |
| A | 12 | HCl | 0.2 | 80–90 | 65 | 78 | <1 | <0.5 | xxx | 60 |
| A | 13 | HCl | 0.2 | 80–90 | 95 | 70 | <0.5 | <0.5 | xxx | 90 |
| B | 14 | HCl | 0.2 | 80–90 | 65 | 78 | 1 | <0.5 | xx(x) | 60 |

I claim:

1. A process for the preparation of 3-acetamido-5-amino-2,4,6-triiodobenzoic acid substantially free from diiodinated material in which 3-acetamido-5-aminobenzoic acid is gradually introduced into an aqueous system by admixture of 3,5-diacetamidobenzoic acid and an excess of iodine chloride stabilized by an inorganic acid or an alkali metal chloride/iodine chloride complex in the presence of inorganic acid, the pH of said aqueous system being below 2.

2. A process as claimed in claim 1 in which the reaction temperature is at least 55° C.

3. A process as claimed in claim 2 in which the temperature is 60°–100° C.

4. A process as claimed in claim 1 in which the pH of the reaction medium is in the range 1 to 0.

5. A process as claimed in claim 1 in which the initial concentration of I Cl is in the range 40 to 120 g/litre, a slight excess over the stoichiometric quantity required for triiodination being present.

6. A process as claimed in claim 1 in which 3,5-diacetamidobenzoic acid and an excess of iodine chloride are added to an aqueous medium containing diacetamidobenzoic acid and acetic acid resulting from the diacetylation of 3,5-diaminobenzoic acid, and the reaction mixture is heated to an appropriate reaction temperature.

10. A process for the preparation of an N-alkyl-3,5-diacetamido-2,4,6-triiodobenzoic acid which comprises preparing 3-acetamido-5-amino-2,4,6-triiodobenzoic acid substantially free from diiodinated material in which 3-acetamido-5-aminobenzoic acid is gradually introduced into an aqueous system by admixture of 3,5-diacetamidobenzoic acid and an excess of iodine chloride stabilized by an inorganic acid or an alkali metal chloride/iodide chloride complex in the presence of an inorganic acid, the pH of said aqueous system being below 2; the 3-acetamido-5-amino-2,4,6-triiodobenzoic acid thus obtained being converted into metrizoic acid or an analogue thereof by N-alkylation to form 3-N-alkylacetamido-5-amino-2,4,6-triiodobenzoic acid which is then acetylated.

* * * * *